United States Patent
Zofchak et al.

(10) Patent No.: US 7,087,700 B2
(45) Date of Patent: Aug. 8, 2006

(54) POLYMERIC URETHANE ESTER TERTIARY AMINES AND RELATED PERSONAL CARE FORMULATIONS

(75) Inventors: Albert Zofchak, Matawan, NJ (US); John Obeji, Clifton, NJ (US)

(73) Assignee: Alzo International, Inc., Sayreville, NJ (US)

( * ) Notice: Subject to any disclaimer, the term of this patent is extended or adjusted under 35 U.S.C. 154(b) by 637 days.

(21) Appl. No.: 10/285,955

(22) Filed: Nov. 1, 2002

(65) Prior Publication Data

US 2004/0086482 A1    May 6, 2004

(51) Int. Cl.
*C08G 18/36* (2006.01)

(52) U.S. Cl. ................ 528/74.5; 528/71; 554/106; 560/26; 560/115; 560/158; 424/70.11; 424/70.28; 424/78.03; 424/78.18

(58) Field of Classification Search ........... 528/74.5, 528/71; 554/106; 560/26, 115, 158; 424/70.11, 424/70.28, 78.03, 78.17

See application file for complete search history.

(56) References Cited

U.S. PATENT DOCUMENTS

| | | | |
|---|---|---|---|
| 4,537,762 A | 8/1985 | Fogel et al. | |
| 4,548,810 A | 10/1985 | Zofchak | |
| 4,940,573 A | 7/1990 | Sebag et al. | |
| 5,674,479 A | 10/1997 | George et al. | |
| 6,315,991 B1 | 11/2001 | Zofchak et al. | |
| 6,392,087 B1 | 5/2002 | Zofchak et al. | |
| 2004/0131573 A1* | 7/2004 | Tang ................ | 424/70.17 |

* cited by examiner

*Primary Examiner*—Rachel Gorr
(74) *Attorney, Agent, or Firm*—Henry D. Coleman; Coleman Sudol Sapone P.C.

(57) ABSTRACT

The present invention is directed to compositions comprising polymeric tertiary amines of urethane esters and salts thereof. The compositions are generally derived from linear or branched chain compounds of synthetic or natural origin, preferably from trialkalnolamines that have been esterified with organic acids including long chain fatty acids and reacted with diisocyanate compounds to form urethane adducts. These adducts are in turn polymerized with organic acids to form polymeric urethane ester tertiary amine salts. The compositions of the present invention may be incorporated into personal care formulations such as cosmetics, toiletries and shampoos and into detergents to improve or modify at least two of the characteristics of such formulations.

25 Claims, No Drawings

POLYMERIC URETHANE ESTER TERTIARY AMINES AND RELATED PERSONAL CARE FORMULATIONS

FIELD OF THE INVENTION

The present invention is directed to compositions comprising polymeric tertiary amines of urethane esters and salts thereof. The compositions are generally derived from linear or branched chain compounds of synthetic or natural origin, preferably from trialkalnolamines that have been esterified with organic acids including long chain fatty acids and reacted with diisocyanate compounds to form urethane adducts. These adducts are in turn polymerized with organic acids to form polymeric urethane ester tertiary amine salts. The compositions of the present invention may be incorporated into personal care formulations such as cosmetics, toiletries and shampoos and into detergents to improve or modify at least two of the characteristics of such formulations.

BACKGROUND OF THE INVENTION

Long chain tertiary amine salts of fatty acids ranging from $C_6$ to $C_{36}$ have been used successfully on a commercial basis and sold under the trade name NECON®. Such compounds are disclosed in U.S. Pat. No. 4,548,810 ("'810 Patent"), the complete disclosure of which is hereby incorporated by reference. These tertiary amine salts have been used in skin and hair contacting formulations in such applications as shaving creams, skin creams, lotions, bar soaps, liquid soaps, body oils, hair colorants, afterbath lotions and splashes, lipsticks, lip balms, bath products and sunscreen formulations for their attributes of assisting in the solubilization of components in these formulations, their conditioning characteristics and their promotion of adherence to the skin and hair. Physical blends of long chain tertiary amine salts and tertiary amine quaternaries ("quats") which have been quaternized with, e.g., dimethyl sulfate, diethyl sulfate, methyl chloride and benzyl chloride have proven effective as compounds which instill favorable characteristics in hair care products.

U.S. Pat. No. 6,315,991 ("'991 Patent") discloses polymeric urethane compounds that exhibit primary utility as surfactants, wetting agents, anti-irritants, conditioners, viscosity builders in shampoos and liquid hand soaps. In addition, compounds of the '991 Patent assist in mending split ends of hair, have low levels of skin, eye and ingestion toxicity and can be used to disperse hair dyes and promote the hair dye function. U.S. Pat. No. 6,392,087 discloses novel compositions of urethane emollients, solubilizers, clarifiers and emulsifiers derived from monohydric alcohols and having no free isocyanate groups. These urethane emollients are substantially free of terminal hydroxyl groups and are derived from linear, branch-chained or aromatic monohydric alcoholic compounds of synthetic or natural origin.

Notwithstanding the utility of the aforementioned long chain tertiary amine salts, tertiary amine quaternary blends, and urethane compositions, there is still the need for a compound or composition which will combine the benefits of these classes of additives to achieve the following: reduced formulation and production cost, increased skin and hair adhesion, greater sheen enhancement and decreased toxicity in the event of ingestion or unintended exposure. Ideally, there is the need for a composition that combines the characteristic benefits attendant to compounds having mono or di-ester and urethane linkages.

OBJECTS OF THE INVENTION

It is an object of the present invention to provide novel polymeric tertiary amine salts of urethane esters that can be used to improve or modify the characteristics of personal care products. Methods for improving or modifying the personal care products are another object of the present invention.

Secondary objects of the invention, depending upon the specific embodiment, may include one or more of the following:

A. To provide polymeric tertiary amine salts of urethane esters for use as conditioners, antistats, detanglers, facilitators for ease of wet/dry combing, to assist in the minimization of split ends (in hair products), as emulsifiers, for the maximization of color in colored hair products (dyes) and for use in detergents.

B. To introduce into hair and skin contacting formulations polymeric tertiary amine salts of urethane esters that will maintain stability and become mildly cationic when used at a pH of less than about 7.0.

C. To increase the "adhesion" of the entire molecule to the hair and skin through the structure of the urethane ester linkages.

D. To provide a basis for "thickening" or increasing viscosity in given hair and skin contacting formulations as a result of the polymeric tertiary amine salt of a urethane ester used.

E. To provide polymeric tertiary amine salts of urethane esters for use as a cosmetic raw material in skin and hair contacting formulations to yield mildness and at the same time have low $LD_{50}$ values.

These and other objects of the present invention may be readily gleaned from the description of the invention that follows.

SUMMARY OF THE INVENTION

In accordance with the above-stated objects, the instant invention provides polymeric urethane ester tertiary amines that may be used in personal care formulations, detergents and fabric softeners. Compositions of the instant invention include polymeric urethane ester tertiary amine salts. Compositions of the present invention may be used as a conditioner, emollient, skin and hair softener. The compounds can be used in skin and hair contacting formulations in the cosmetic, toiletry and personal care product field. The introduction of mono-, di- and/or tri-ester linkages in the compounds of the present invention, combined with the adhesion characteristics of the urethane linkages present in the compounds, yield enhanced properties which have thus far been unachievable with regard to the development of end products. For example, the compounds can serve as a high sheen conditioner with excellent wet/dry comb properties that surpass the properties of known individual ester or quat products. By combining the ester, urethane and amine functionality within one compound, it is possible to make end use formulations with outstanding characteristics using one, as opposed to several, additives.

The compositions of the instant invention are useful in many application areas within the cosmetic, toiletry, personal care, detergent and fabric softening industries. The innovative compositions of the present invention are based on ester and urethane chemistry and combine attributes as taught by Zofchak in *Methods of Lubricating the Skin* (Zofchak) based on tertiary amine salt derivatives of long chain fatty acids.

Compositions of long chain tertiary amine salts as taught by Zofchak have been reacted with long chain fatty acids have become extremely successful and useful in numerous areas of the cosmetic, toiletry and personal care industries wherein substantial markets have been developed in the following end use areas:

| | |
|---|---|
| A. | Lipsticks |
| B. | Hair Coloring Products |
| C. | Liquid Soaps |
| D. | Bar Soaps |
| E. | Creams and Lotions |
| F. | Bath Gels |
| G. | Hand Cleaners |
| H. | Conditioners |
| I. | Shampoos |
| J. | Detanglers; for Hair |
| K. | Fabric Softeners |

Polymeric urethane ester tertiary amines and salts thereof of the instant invention are made by reacting an organic acid (defined hereinafter) with a urethane adduct formed by reacting a diisocyanate with a monomeric or polymeric mono-, di-, or tri-ester of a trialkanolamine. ("Tertiary amines" as used herein includes ditertiary amines). The compositions of the instant invention can be made one-pot or in steps. Monomeric or polymeric mono-, di-, or tri-esters of trialkanolamines are made by esterifying a trialkanolamine of formula (I):

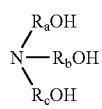

(I)

where $R_a$, $R_b$ and $R_c$ are the same or different and are substituted or unsubstituted, branched or unbranched alkyl groups derived from an alkanolamine, with an organic acid (as defined hereinafter) having one or more carboxyl groups to form a monomeric or polymeric mono-, di-, or tri-ester. The reaction temperature for this esterification may be about 30° to about 300° C., and is preferably about 170° to about 220° C.; the reaction pressure may be about 3 to about 3,000 mbar, and is preferably about 700 to about 1,100 mbar. It is also possible to use elevated temperatures and pressures, but this is generally not necessary. The esterification catalysts employed can include, inter alia, alkali metal hydroxides, mineral acids and Lewis acids. Examples of trialkanolamines useful in making polymeric tertiary amine salts of urethane esters of the instant invention are triethanolamine, triisopropanolamine, triisobutanolamine, triisopentanolamine, trilsohexanolamine, diethanolmonoisopropanolamine, monoethanoldiisopropanolamine, monoethanoldiisobutanolamine and their analogues.

Preferred organic acids that may be reacted with these trialkanolamines include long chain fatty acids selected from the group consisting of $C_2$ to $C_{36}$ dimer and trimer acids, alpha hydroxy acids, beta hydroxy acids, linear acids, isomeric acids and phenylstearic acids. Compositions of the present invention also include esters derived from linear $C_6$ through $C_{22}$ fatty acids, $C_6$ through $C_{22}$ isomeric acids, aromatic acids, phenylstearic acids, dimer acids as well as trimer acids which range from 36 through 48 carbon chain lengths.

For example, a monomeric diester formed by the reaction of a monocarboxylic acid with the trialkanolamine in a 2:1 molar ratio of acid to trialkanolamine is represented by formula (II)

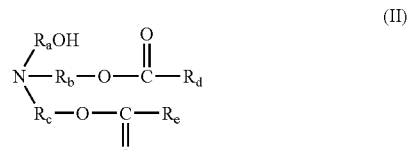

(II)

where $R_a$, $R_b$ $R_c$ are as previously defined and $R_d$ and $R_e$ are the same or different and are a $C_2$ through $C_{48}$ (preferably, $C_6$ through $C_{22}$) linear or branched-chained, cylic, saturated or unsaturated hydrocarbon group which is substituted, monomeric or dimeric or an aromatic group, including a phenyl or benzyl group or substituted phenyl or benzyl group, an alkylphenyl, alkylbenzyl, substituted alkylphenyl or alkylbenzyl group, any of which may contain one or more ester or hydroxyl groups or urethane linkages. Alternatively, a polymeric ester may be formed by the esterification of a trialkanolamine of formula (I) with a polycarboxylic organic acid.

The extent of mono, di-, or tri-ester polymerization is determined by the number of hydroxyl-terminated groups available for esterification by the carboxyl groups within the polycarboxylic acid and by the molar ratio of trialkanolamine relative to polycarboxylic acid. For example, where $C_6$ through $C_{22}$ monocarboxylic acids are used to esterify the alkanolamine, the resultant mono or diesters are part of a structure wherein the ester itself is monomeric in nature. If dimer or trimer acids (organic acids with multi-carboxylic functionality) are used to esterify the trialkanolamine, a polymeric trialkanolamine ester will be formed. In either instance, the monomeric or polymeric mono, di-, or tri-ester must contain a free (unreacted) hydroxyl group for subsequent urethane linkage formation (in the case of the tri-ester, an unreacted hydroxyl group from the polycarboxylic acid), which is achieved as follows.

Urethane adducts are formed by reacting the monomeric or polymeric mono-, di-, or tri-esters in the presence of heat and either an amine or tin catalyst such as stannous octanoate with a diisocyanate of the formula $R_f$—$(N=C=O)_2$, where $R_f$ is a saturated, unsaturated, aromatic or halogen substituted linear, cyclic, aromatic or branch-chained hydrocarbon; each isocyanate moiety is thereby either converted to a urethane moiety or becomes a side chain substituent available for urethane linkage formation and the urethane adduct of the monomeric or polymeric mono-, di-, or tri-ester ester is formed. Isophorone diisocyanate (IPDI) is particularly preferred as the diisocyanate. Urethane adduct formation reaction temperatures can range from slightly above room temperature, i.e., 50° C. to about 150° C. or more, preferably around 50° C. to 100° C. For example, the urethane adduct of the monomeric di-ester of Formula (II) is represented by the following formula (III):

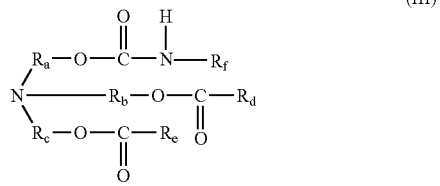

(III)

where $R_a$ through $R_f$ are as previously defined. The molar ratio of polymeric mono-, di-, or tri-esters to diisocyanate can be varied to form a different number of urethane linkages depending upon the number of hydroxyl terminated groups available in the mono-, di-, or tri-ester for reaction with the diisocyanate.

These urethane adducts form mono or di-tertiary amine salts by reaction with a mono-, di- or tri-carboxylic acids of the formula $R_g(OOH)_n$, where n is 1 to 3 and $R_g$ is the same as or different from $R_d$ or $R_e$ and is selected from $C_4$ through $C_{48}$ (preferably, $C_6$ through $C_{22}$) linear or branched-chained, cylic, saturated or unsaturated hydrocarbon groups which are substituted, monomeric or dimeric or an aromatic group, including a phenyl or benzyl group or substituted phenyl or benzyl group, an alkylphenyl, alkylbenzyl, substituted alkylphenyl or alkylbenzyl group, any of which may contain one or more ester or hydroxyl groups or urethane linkages. Reaction temperatures for the formation of the mono or di-tertiary amine salts can range from as low as 30° C. to as high as 150° C. or more.

In preferred embodiments, $C_6$ through $C_{36}$ fatty acids such as linear, isomeric, aromatic, dimerized or trimerized fatty acids, including alpha hydroxy and beta hydroxy acids, are reacted to form mono- or ditertiary amine salts of polymeric urethane esters. Urethane adducts made in accordance with the instant invention and comprising $C_5$ through $C_{36}$ mono or diesters of linear, isomeric, aromatic and dimer acid derivatives may be reacted with a $C_6$ through $C_{36}$ fatty acid such as a linear, isomeric, aromatic, dimerized or trimerized fatty acid, including alpha hydroxy and beta hydroxy acids, to form a tertiary amine salt of the urethane adduct. Preferably, each of $R_d$, $R_e$ and $R_g$ are linear or branched-chain, saturated or unsaturated, alkyl or alkylene groups which are derived from organic acids (as defined hereinafter), most preferably from fatty acids of natural original. Preferred hydroxyl containing acids for use in the present invention include ricinoleic acid and 12-hydroxystearic acid. Other organic acids useful in making compositions of the instant invention include but are not limited to alpha hydroxy and beta hydroxy organic acids such as lactic, hydroxy caprylic, hydroxy capric and salicylic acids, among numerous others.

Examples of compounds that have been prepared according to the present invention are the reaction product of TEA Linoleate/Ricinoleate Diester/IPDI Copolymer with oleic acid: (INCI Name: TEA Diricinoleate/IPDI Copolymer with oleic acid) and the reaction product of TEA Ricinoleate Diester/IPDI Copolymer with dilinoleic acid (INCI Name: TEA ricinoleate/IPDI copolymer with dilinoleic acid).

In making the tertiary amine salts of the instant invention, the molar ratio of the polymeric tertiary amine urethane ester adduct to organic acid should be less than one. To provide a composition that is as nonirrating as possible, it is preferable to use a smaller molar excess of a stronger acid relative to the urethane adduct as opposed to a larger molar excess of a weaker acid relative to the adduct.

Through a unique combination of urethane and tertiary amine chemistry provided by the invention, polymeric compositions of the instant invention may propagate through ester or urethane linkages added along their backbone or through side chain addition. The compounds may be unsubstituted or substituted (generally, halogen or hydroxyl substituted), but preferably are only hydroxyl substituted. The linear backbone of compositions of the present invention may be totally saturated or contain exclusively single bonds (fully saturated) or at least one double or triple bond (unsaturated) which affect the solubility and viscosity of the final product.

As will be seen, any number of useful compositions of varying size and structure may be obtained by the present invention, depending upon the selection and amounts of the following used during composition synthesis: (1) the alkanolamine; (2) the organic acid; and (3) the diisocyanate. Variation of these parameters may result in compositions of the instant invention that are or are not substantially substantially free of hydroxy terminated end groups, as defined hereinafter.

Additional aspects of the instant invention are presented in the following detailed description.

DETAILED DESCRIPTION OF THE INVENTION

The following definitions shall be used throughout the specification in describing the present invention.

The term "alkanolamine" means a water soluble, viscous amino alcohol of the aliphatic series; "trialkanolamine" as used herein means a tri-substituted amino alcohol such as triethanolamine.

The term "aliphatic series" means the series of open-chain carbon and hydrogen compounds with saturated or unsaturated bonds.

The term "carboxylic acid" as used herein describes organic acids which may contain one or more carboxylic acid moieties preferably ranging in size from $C_2$ to $C_{50}$ or more. The term "monocarboxylic acid" is used to describe organic acids that contain only one carboxylic acid moiety. The term "polycarboxylic acid" is used to describe organic acids which contain at least two carboxylic acid moieties. Those polycarboxylic acids which contain only two carboxylic acid moieties, subsumed under the general "polycarboxylic acid" label, may also be referred to in this specification as "dicarboxylic acids". Carboxylic acids may also be generated from anhydrides such as acetic anhydride, maleic anhydride, among numerous others.

Exemplary carboxylic acids for use in the present invention include, for example, pentanoic acid, neopentanoic acid, caproic acid, caprylic acid, capric acid, heptanoic acid, neoheptanoic acid, octanoic acid, iso-octanoic acid, 2-etlhylhexanoic acid, nonanoic acid, isononanooic acid, decanoic acid, iso-decanoic acid, neodecanoic acid, undenanoic acid, undecylenic acid, lauric acid, isolauric acid, myristic acid, palmitic acid, stearic acid, hydroxy stearic acid, isostearic acid, arachidonic acid, tallow fatty acid, arachidic acid, behenic acid, lignoceric acid, lauroleic acid, myristoleic acid, palmitoleic acid, olelic acid, gadoleic acid, erusic acid, ricinoleic acid, linolenic acid, linoleic acid, lactic acid, glycolic acid, mandelic acid, eicosopentaoic acid, phenylstearic acid, retinoic acid, salicylic acid and benzoic acid, among numerous others, including dimer acids, trimer acids, adipic acid, azealeic acid, malic acid, succinic acid, dodecandioic acid, citric acid, tartaric acid, sebacic acid, fumaric acid, glucaric acid, glutaric acid and oxalic acid, among others.

Preferred polycarboxylic acids for use in the present invention include, for example, $C_2$–$C_{50}$ dicarboxylic acids, including dimer, trimer and tetramer acids which are made from the dimerization, trimerization or tetramerization of long-chain unsaturated acids, such as linoleic acid, among numerous other acids, including mixtures of these acids, more preferably including $C_5$–$C_{37}$ dicarboxylic acids and mixtures of these acids. Dilinoleic acid is a preferred dicarboxylic acid. Other acids, which may be preferably used in the present invention, include, for example, adipic acid, azealeic acid, malic acid, succinic acid, dodecandioic acid, citric acid, tartaric acid, sebacic acid, fumaric acid, glucaric acid, glutaric acid and oxalic acid, among others. Preferred dicarboxylic acids containing carboxylic groups at the terminal ends of the molecule.

Other exemplary polycarboxylic acids include, for example, polymeric products which contain carboxylic (carboxylate) side chains, such as acrylic or (meth)acrylic, polyesters, cellulosic polymers, polysiloxanes, oligo and polypeptides, among numerous others.

The term "diisocyanate" is used throughout the specification to describe a linear, cyclic or branch-chained hydrocarbon having two free isocyanate groups. The term "diisocyanate" also includes halogen substituted linear, cyclic or branch-chained hydrocarbons having two free isocyanate groups. Exemplary diisocyanates include for example, isophorone diisocyanate, m-phenylenediisocyanate, p-phenylene diisocyanate, 4,4-butyl-m-phenylene diisocyanate, 4-methoxy-m-phenylene diisocyanate, 4-phenoxy-m-phenylene diisocyanate, 4-chloro-m-phenylene diisocyanate, toluenediisocyanate, m-xylylenediisocyanate, p-xylylenediisocyanate, 1,4-napthalenediisocyanate, cumene-14,-diisocyanate, durenediisocyanate, 1,5-napthylenediisocyanate, 1,8-napthylenediisocyanate, 1,5-tetrahydronapthylenediisocyanate, 2,6-napthylenediisocyanate, 1,5-tetrahydronapthylenediisocyanate; p,p-diphylenediisocyanate; 2,4-diphenythexane-1,6-diisocyanate; methylenediisocyanates; ethylenediisocyanates; trimethylenediisocyanate, tetramethylenediisocyanate, pentamethylenediisocyanate, hexamethylenediisocyanate, nonamethylenediisocyanate, decamethylenediisocyanate, 3-chloro-trimethylenediisocyanate and 2,3-dimethyltetramethylene diisocyanates.

The term "fatty acid" means monobasic acids containing only the elements carbon, hydrogen and oxygen and consisting of an alkyl radical attached to the carboxyl group having at least 8–10 carbon atoms in the molecule. "Fatty acid" as used herein includes saturated fatty acids of the formula $C_n H_{2n} O_2$, as well as unsaturated fatty acids of the oleic acid series $C_n H_{2n-2} O_2$, the linoleic acid series $C_n H_{2n-4} O_2$ and the linolenic acid series $C_n H_{2n-6} O_2$, as well as fatty acids with four or more double bonds, fatty acids with hydroxyl groups in the molecule and fatty acids containing cyclic groups. Further, fatty acids as used herein includes linear, isomeric, aromatic, dimerized and trimerized fatty acids including alpha hydroxy, beta hydroxy acids as well as a number of anhydrides, linear or branched-chain saturated or unsaturated alkyl or alkylene groups which are derived or obtained from fatty acids or fatty amines of natural original, most preferably, fatty amines obtained from plant sources.

The term "organic acid" means carboxylic acids, fatty acids, $C_6$ through $C_{22}$ isomeric acids, aromatic acids, phenylstearic acids, dimer acids and $C_{36}$ to $C_{48}$ trimer acids. Preferred organic acids include oleic acid, stearic acid, palmitic acid, coconut fatty acid, lauric acid, myristic acid, arachidonic acid, erusic acid, ricinoleic acid, ricinleic acid, 12-hydroxystearic acid, caproic acid, capric acid, monoricinoleic, di-ricinoleic, mono-12-hydroxystearic, di-12-hydrostearic, monobehenic, dibehenic, monooleic, di-oleic, mono-soya, di-doya, mono-safflower, di-safflower, monosunflower, disunflower, mono-myristic and di-myristic acids.

The term "emollient" is used throughout the specification to describe compounds according to the present invention which soften, lubricate and moisturize the skin as as well as sooth irritation to the skin and mucous membranes, i.e., they are soothing to the skin.

The term "emollient effective amount" is used throughout the specification to describe concentrations or amounts of compounds according to the present invention which are included in cosmetic and personal care products according to the present invention which provide effective emollient character for treating keratinous and epithelial tissue, including skin, nails (ungual tissue), hair and mucous linings of the mouth and nasal passages.

The term "effective amount" is used throughout the specification to describe concentrations or amounts of compounds according to the present invention which are effective in conveying desired traits such as emulsification, clarification, adhesion, melting point modification or solubility to a formulation of a cosmetic, toiletry or personal care product.

The term "substantially free" is used throughout the specification to describe preferred urethane compounds according to the present invention which essentially contain no free terminal hydroxyl groups or cyanide groups, i.e., they appear to be all reacted and analytical methods do not detect terminal hydroxyl groups other than those which may appear as slight impurities in the compounds of the present invention. The term "substantially free" is not a theoretical absolute value, but merely reflects the practical limits of detecting free terminal hydroxyl groups in the present invention.

The term "personal care product" is used throughout the specification to describe a cosmetic or toiletry product which is preferably used on or in contact with the hair, skin and/or nails and which include effective concentrations of one or more of the compositions according to the present invention. Personal care products include, for example, cosmetics, floating bath oils, after shaves, creams, lotions, deodorants, including stick deodorants, pre-electric shave lotions, after-shave lotions, antiperspirants, shampoos, conditioners and rinses and related products, among others, including skin care products, eye makeups, body shampoos, protective skin formulations, lipsticks, lip glosses, after-bath splashes, pre-sun and sun products, including sunscreens. Virtually any chemical product which comes into contact with the hair or skin and which may include effective amounts or concentrations of one or more of the compositions according to the present invention may be considered a personal care product according to the present invention.

The term "surfactant" is used throughout the specification to describe compounds according to the present invention which contain a tertiary amine group which has been further reacted to form or otherwise forms an N-oxide group, a quaternary amine group or a carboxylate salt. Certain compounds according to the present invention are also referred to as urethane betaines, urethane N-oxides or urethane quaternary compounds because of the existence of at least one betaine group, N-oxide group or quaternary group (preferably more than two) and at least one urethane group (preferably, at least two).

The term "hydrocarbon" is used throughout the specification to describe various substituent groups according to the present invention. The term hydrocarbon embraces, but is not limited to, for example, alkyl, alkene groups (including those groups containing more than one unsaturated double bond), alkyne groups, aryl groups, aralkyl groups and related groups which are comprised of carbon and hydrogen atoms, such as alkylene groups (which are similar to alkyl groups except they are substituted at two carbons of the hydrocarbon with atoms or substituents other than hydrogen rather than one as is the case with alkyl groups) and related hydrocarbon radicals which may be found in the present compositions. In certain cases the terms "alkyl" (or related alkyl groups such as methyl, phenyl, benzyl, etc.) is used interchangeably with a di-substituted hydrocarbon group such as an alkylene, methylene, phenylene, etc. Hydrocarbons according to the present invention may be linear, cyclic or branch-chained, substituted (i.e., have pendant halogen, hydroxyl or other groups) or unsubstituted (i.e., comprised exclusively of C and H atoms) monomeric or dimeric (or even of higher order), aromatic, including phenyl or benzyl or substituted phenyl or benzyl group, alkylphenyl, alkylbenzyl or substituted alkylphenyl or alkylbenzy groups.

The term "hydroxyl terminated" refers to an end group on the compositions according to the present invention that contains a free hydroxyl group at its terminal end. Although hydroxyl terminated groups are primarily and preferably primary hydroxyl groups, the terminal hydroxyl group may be found in a position such that the hydroxyl group is also a secondary or even a tertiary hydroxyl group. Hydroxyl terminated groups in compositions according to the present invention may be further reacted with carboxylic acids to form esters or isocyanates to form urethane groups as more fully described herein.

The term "tertiary amine" is used to describe an amine to which is attached at least three carbon-containing groups, each of the groups being covalently bonded to the amine group through a carbon atom within the group.

The term "substituents" ("substituted") means compositions may include for example, halogens such as fluorine, chlorine and bromine, nitro groups, amine groups, substituted amine groups, hydroxyl groups, alkoxy groups, unsubstituted and substituted alkoxy groups, alkyl groups or substituted alkyl groups, among numerous others. Preferably, the substitutents in the present compositions are limited to halogen groups, most preferably fluorine and chlorine. One of ordinary skill in the art will be able to recognize modifications which readily may be made to the present compositions to instill desirable characteristics in the present compositions and to avoid undesirable reactions during polymerization such as chain termination, crosslinking and other reactions which may occur with reactive substituents such as hydroxyl groups and amines or amine-containing groups.

Compositions according to the present invention may vary widely in size over a broad range. The chain length of individual polymeric units (i.e., esterified alkanolamine and reacted diisocyanate) of preferred compositions of the present invention may range from about 25 carbon atoms in the backbone to about 200 carbon atoms in the backbone with a preferred chain length of a polymeric unit being in the range of about 40 to 120 carbon atoms in the backbone.

A tertiary amine salt of a ricinoleic urethane adduct is made in accordance with the instant invention as follows. A ricinoleic urethane adduct may be formed by the esterification of triethanolamine (TEA) by reaction with ricinoleic acid (a fatty acid with one carboxyl group) to form a monomeric TEA diester, which in turn is reacted with isophorone diisocyanate (IPDI) in a molar ratio of one mole of monomeric TEA diester to one mole of IPDI form the urethane adduct. The number of urethane linkages added to the monomeric diester can be increased by increasing the molar ratio of IPDI to monomeric TEA diester such that unreacted IPDI reacts to form urethane linkages with the hydroxyl terminated groups on the ester side chain or by virtue of reaction of such hydroxyl groups with an available isocynate group incorporated into the side chain or back bone by the condensation reaction of IPDI and a hydroxyl group. The urethane adducts can be reacted, e.g., with a $C_6$ through $C_{36}$ fatty acid such as a linear, isomeric, aromatic, dimerized or trimerized fatty acid, including alpha hydroxy and beta hydroxy acids, to form the tertiary amine salt of the ricinoleic urethane adducts.

Similarly, 12-hydroxystearic acid may be used to esterify TEA to form a monomeric or polymeric TEA mono or di-ester, which can be reacted with IPDI to yield a urethane adduct. Preferably, the monomeric di-ester/IPDI molar ratio is about 1:2, which will yield a urethane adduct (compound XI, below), which may be further reacted with a $C_6$ through $C_{36}$ fatty acid such as a linear, isomeric, aromatic, dimerized or trimerized fatty acid, including alpha hydroxy and beta hydroxy acids, to form a tertiary amine salt of the hydroxystearic urethane adduct. Other compositions according to the present invention may follow similar reaction approaches.

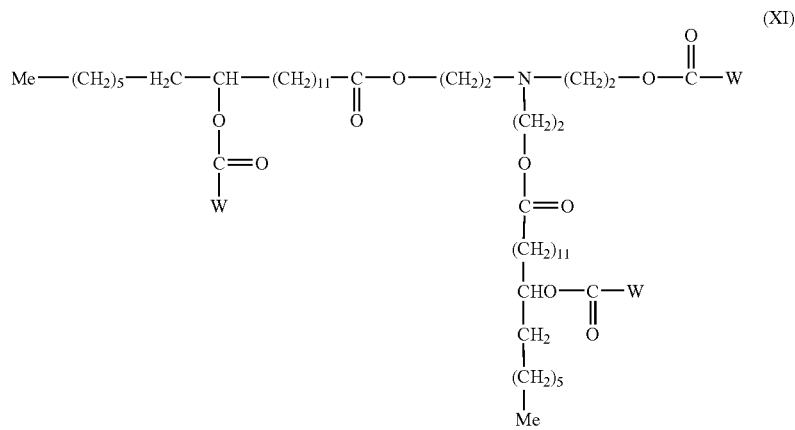

It has also been surprisingly found that mono and/or diesters of alpha hydroxy and beta hydroxy carboxylic acids such as lactic, hydroxy caprylic, hydroxy capric and salicylic acids, can be esterified to a mono- or difunctionality with a trialkanolamine to yield urethane adducts in accordance with the instant invention. These adducts can be polymerized with a diisocyanate such as isophorone diisocyanate and reacted with a mono, di or tricarboxylic acid to yield the corresponding tertiary amine salt of the urethane adduct.

Compositions of the instant invention exhibit primary utility as surfactants, wetting agents, anti-irritants, conditioners, viscosity builders in shampoos, detergents and liquid hand soaps. In addition, they assist in mending split ends of hair, have low levels of skin, eye and ingestion toxicity and can be used to disperse hair dyes and promote the hair dye function.

By selecting the diisocyanate, using the appropriate chain length, taking the degree of unsaturation in the backbone and by adjusting the degree of esterification, it is possible to introduce water solubility/insolubility or emulsification characteristics to the polymer. And, by building a polymeric surfactant based on amine and urethane technology, it is possible to offer a product that has substantiality to both the skin and hair based on the urethane bonds. Furthermore, adhesion and substantiality of the molecule may be enhanced by the cationic structure of the composition which becomes more cationic with decreasing pH. Additionally, these polymeric amine urethane esters are compatible with a wide array of surfactants that are commonly used in the cosmetic and toiletry industry such as amides, amine oxides, sulfosuccinates, sulfonates, sulfated castor oil, etc., since they share similar backbones.

Other properties and characteristics of the compounds of the present invention which make them highly desirable to the cosmetic and toiletry industry are as follows:

A. Extremely low order of toxicity and irritation
B. Low color
C. Low odor
D. Excellent compatibility in cosmetic formulations
E. Solubility with amides, sulfonates sulfosuccinates, and sulfobetaines
F. Nonrancidification
G. Coupling characteristics
H. Solubility in water, glycols and lower molecular weight alcohols
I. Ability to be synthesized to become insoluble in water, glycols and lower molecular alcohols (propoxylated versions)

Effective amounts of the polymeric tertiary amine urethane adducts of the present invention may also function as coupling and clarifying agents in formulations in the personal care, toiletry and cosmetic industry, where glycols with their inherent viscosity reduction properties have been used in the past. The novel tertiary amine urethane polymers may effectively replace ethoxylated sorbitan monoesters of lauric and/or oleic acids for their clarification, coupling and solubilization properties. Additionally, the products of the present invention are naturally derived, are biodegradable and are compatible with biological systems and demonstrate a low order of toxicity and irritation.

The present compounds inherently bestow upon a cosmetic formulator the ability to achieve a wide range of desirable end characteristics that may be sought in a given formulation by selecting polymeric urethanes according to the present invention and adding it to a composition to be improved or modified. Indeed, it is an unexpected result of the present invention that personal care products may have at least two characteristics, and often, more than two characteristics of the formulation substantially modified by the introduction of a single composition. By selecting a backbone with increased unsaturation, it is possible not only to increase water solubility but also to decrease viscosity of the polymeric tertiary amine urethanes. The higher the degree of unsaturation present in the molecule, the greater the effectiveness of softening, conditioning, prevention of flyaway hair and increased benefits of wet and dry combing, etc. As one increases both the number of urethane groups within the composition, the molecular weight of the composition will increase as will the viscosity (generally) and ability of the composition to adhere to keratinous tissue. Those of ordinary skill engaging in routine experimentation will be able to determine the preferential chain lengths for optimum results. Beneficial characteristics for foaming are to be found in the $C_{12}$ through $C_{18}$ chain lengths. Chain lengths primarily ranging from $C_{18}$ through the $C_{22}$ area will tend to have a greater effect upon viscosity of a given formulation.

Compositions according to the present invention may be used to formulate skin and hair contacting formulations in the cosmetic, toiletry and personal care industries that have excellent aesthetics heretofore unachievable. They will exhibit improved emulsification, detangling, conditioner, softening, prevention of flyaway hair and antistatic characteristics and will facilitate wet and dry hair combing and repair of split ends (hair). Further, the surfactants so derived also will assist in hair colorization and are of a low order of dermal and ocular toxicity. The combination of characteristics which can be instilled in a personal care product using a single composition according to the present invention without relying on numerous additives is unexpected. That all of these characteristics could be instilled with a substantial absence of toxicity is particularly unexpected.

The compositions of the present invention will also serve as excellent hair conditioners or detergent additives and show effectiveness in the following systems: shave creams; women's toiletries for shaving preparations; depilatories; relaxers; conditioners; and 2-in-1 shampoos. Furthermore, the present invention will provide the following personal care formulation benefits: reduce split ends in conditioning and shampoo formulations; provide good wet/dry combing; provide body and shine to hair; reduce tangles and provides a more manageable base for styling; soften coarse hairs to provide easier shaving; and provide a closer, less damaged shave.

In general, compositions according to the present invention are included in personal care products/formulations in effective amounts, i.e., amounts which produce an intended effect. The amount of composition generally ranges from about 0.05% to about 15% by weight or more of personal care formulations according to the present invention. In preferred embodiments of emulsion-based formulations, compositions according to the present invention are included in amounts ranging from about 0.1% to about 5% by weight. In the case of shampoos and conditioners, compositions according to the present invention are included in amounts ranging from about 0.1% to about 3% by weight of the formulation.

For example, in shampoos, rinses, conditioners, hair straighteners, hair colorants and permanent wave formulations, the compositions according to the present invention preferably comprise about 0.1% to about 20% by weight, more preferably about 0.25% to about 3% by weight of the final end-use hair-care composition. Other components which may be included in hair-care formulations include, for example, a solvent or diluent such as water and/or alcohol, other surfactants, thickeners, coloring agents, preservatives, additional conditioning agents and humectants, among numerous others.

In the case of shave creams and gels, after-shave lotions and shave-conditioning compositions (for example, pre-electric shave formulations), the compositions according to the present invention are included in amounts ranging from about 0.25% to about 15% or more by weight, more preferably about 0.5% to about 10% by weight. Other components which may be included in these end-use compositions include, for example, water, and at least one or more of emollients, humectants and emulsifiers and optionally, other conditioning agents, medicaments, fragrances and preservatives.

In the case of skin lotions and creams, the present compositions are included in amounts ranging from about 0.25% to about 15% by weight, more preferably, about 0.5 to about 10% by weight. Additional components which may be employed in these compositions include, for example, water, emollients and emulsifers and optionally, other conditioning agents medicaments, fragrances and preservatives.

In the case of sunscreens and skin-protective compositions, the present compositions are included in amounts ranging from about 0.25% to about 15% or more by weight, preferablyt about 0.5% to about 7.5% by weight of the final formulations. Additional components which may be employed in these compositions may include, for example, a UV absorbing composition such as para-amino benzoic acid (PABA) or a related UV absorber or a pigment such as $TiO_2$, water or oil, and optional components including, for example, one or more of an oil, water, suspending agents, other conditioning agents and emollients, among others.

In the case of bar and liquid soaps, compositions according to the present invention are included in amounts ranging from about 0.25% to about 20% by weight or more, preferably about 0.5% to about 10% by weight. Additional components which may be included in bar and liquid soaps include water and surfactants and optionally, bacteriacides, fragrances and colorants, among others.

When the present invention is used in a shave cream it will provide the following: closeness of shave; less damage; softer skin feel; longer lasting fragrance; smoother shave; and ease of shave.

When introduced into 2:1 conditioning shampoos and into hair conditioners, the present invention yields excellent conditioning of damaged hair; and, in fact, performs better than commercially available products in the marketplace. Furthermore, the present invention when incorporated into both shampoos and conditioners, should yield the following effects: better "feel"; better appearance; and increased viscosity.

Also, formulations of the instant invention will perform better than normal allowing the formulator to reduce the maximum temperature of the phases, thereby decreasing manufacturing time and, in effect, reducing costs.

The present invention is now described, purely by way of illustration, in the following examples. It will be understood by one of ordinary skill in the art that these examples are in no way limiting and that variations of detail can be made without departing from the spirit and scope of the present invention.

EXAMPLES

Materials and Methods

In performing the following syntheses and preparing the following final formulations, the reagents which are used are indicated in the specific examples. Solvents, where used, are preferably distilled prior to use. Sources of other materials are indicated in the appropriate experimental section. In most instances, although not in every instance, trademarked materials are available from Alzo, Inc., Sayreville, N.J.

Laboratory Procedures

Example 1

Laboratory Procedure for Reaction Product of TEA Linoleate/Ricinoleate Diester/IPDI Copolymer with Oleic Acid To one mole of triethanolamine, 99% purity, is added two moles of ricinoleic acid in a three-neck 1 liter flask equipped with heat, agitation and nitrogen. To this mixture is added approximately 1 gram of dibutyl tin dilaurate, and the mixture is heated to approximately 170° C. to 225° C. to achieve complete esterification which is measured by the acid number as well as through a determination of the grams of water liberated by the reaction.

The above product is dried and defined by the following specifications:

| | |
|---|---|
| Appearance | Clear, Amber Viscous Liquid |
| Color, Gardner | 7 |
| Odor | Characteristic |
| Specific Gravity @ 25° C. | 1.4786 |
| Acid Value | 2.0 |
| Alkali Value | 74.5 |

The above diester with an approximate molecular weight of 934 is placed in a three-neck 2 liter flask equipped with heat, agitation and a nitrogen blanket and dried under 25 inches of vacuum and cooled to approximately 70° C. Approximately 66 grams of IPDI is added added over a three-hour period. The reaction is monitored on infrared to determine the completion of the reaction of the two indicated reactants. The product is defined as follows:

| | |
|---|---|
| Appearance @ 25° C. | Amber Viscous Liquid |
| Color, Gardner | 7+ |
| Odor | Mild |
| Alkali Value | 74. |

The above indicated triethanolamine Diricinolate/IPDI Copolymer is neutralized with dimer acid as follows:

Approximately 515 grams of the TEA Diricinoleate/IPDI Copolymer is placed into a three-neck 1 liter flask and brought to a temperature of 50° C. to 75° C. Approximately 155 grams of dimer acid is slowly added over a two- to three-hour period and monitored for free amine until the reaction has been completed. It is preferential to have an acid number of approximately 45 maximum to ensure there is no unreacted tertiary amine.

| | |
|---|---|
| Color, Gardner | Clear Amber Viscous Liquid |
| Odor | Characteristic |
| pH of 1.0% Dispersion | 6.8 to 7.0 |

Propylene glycol or hexylene glycol or similar diluents may be added to the above polymeric urethane ester tertiary amine dimerate. Concentrations of such diluents may vary from 10 to 60% of the total weight of the final product.

Example 2

Polyurethane from TEA Linoleic Acid/Ricinoleic Acid Mixture

To one mole of 99% TEA is added one mole of linoleic acid and one mole of ricinoleaic acid into a three-neck one liter flask equipped with agitation, heat and a nitrogen blanket. The reaction is catalyzed by hypophosphorous acid and heated to a temperature of about 160–200° C. Water is taken off as water of esterification until the acid number of 2.0 maximum is achieved. A vacuum of 25 inches may be applied to drive the reaction to completion.

One mole of the TEA linoleate/ricinoleate ester is placed into a one liter three-neck flask equipped with heat, agitation and a nitrogen blanket and heated to 125° C. and dried with a vacuum of 25 inches of mercury. The mixture is then cooled to approximately 60° C. and one mole of IPDI is slowly dropped into the flask with good agitation over a temperature range that may reach 120° C. The addition may occur over a two-hour period, and the mixture is then held at 70° C. and the cyanate peak is monitored on infrared until it is no longer detectable. The mixture is held for an additional two hours and is then ready for the next step.

One mole of the TEA Linoleate/Ricinoleate Diester/IPDI copolymer is placed into a three-neck one liter flask and heated to a temperature of 40° C. Through an additional funnel 1.025 moles of oleic acid is added over a two-hour period, during which time the temperature may exotherm to 60° C. to form the ditertiary amine salt of the TEA Linoleate/Ricinoleate/IPDI copolymer.

Example 3

Formulary

Pre-Electric Shave Lotion

| Raw Material | %. Weight. | INCI Name |
|---|---|---|
| Water (Deionized) | 59.90 | Aqua |
| Phenoxyethanol and Methyl Paraben and Propyl and Ethyl Parben and Butyl Paraben | 0.2 | Same as on Left |
| Glycereth-26 | 10.0 | Glycereth-26 |
| TEA Diricinoleate/IPDI Copolymer Dimer Dilinoleate | 1.0 | Same as on Left |
| Neopentyl Glycol Dicaprate | 14.5 | Neopentyl Glycol Dicaprate |
| Potassium Cetyl Phosphate | 1.15 | Potassium Cetyl Phosphate |
| Water (Deionized) | 1.0 | Aqua |
| Triethanolamine, 99% | 1.0 | Triethanolamine |
| SD 40 Alcohol | 10.0 | SD Alcohol 40 |
| Water (Deionized) | 1.0 | Aqua |
| Imidazolinyl Urea | 0.25 | Imidazolinyl Urea |
| Total | 100.0 | |

Procedure:

1. To a clean reaction vessel add water and Phenoxylethanol Preservative blend and heat to 80° C.
2. Combine the Glycereth-26 and TEA Diricinoleate/IPDI Copolymer and introduce to water/preservative blend of step 1.
3. Combine the Neopentyl Glycol Dicaprate and Potassium Cetyl Phosphate and heat to 80° C. and add to the reaction product of Steps 1 and 2.
4. Cool the batch to 50° C. and slowly add the SD 40 Alcohol and cool to 35° C.
5. Add the remaining Water and Imidazolinyl Urea to blend and reduce temperature to 25° C.

Results: The above-described Pre-Electric Shave Lotion is applied to bearded face and permitted to dry before shaving with an electric shaver. The result is an exceptionally smooth shave with little or no friction from cuts, scratches or knicks.

Example 4

Hair Conditioner

| RAW MATERIAL | %. WT. | INCI NAME |
|---|---|---|
| Water (Deionized) | 91.7 | Aqua |
| Methyl Paraben | 0.2 | Methyl Paraben |

-continued

| RAW MATERIAL | %. WT. | INCI NAME |
|---|---|---|
| Behenyl Dimethylaminopropyl Amine Behenate | 0.2 | Same as on Left |
| Hydroxyethyl Cellulose | 1.0 | Hydroxyethyl Cellulose |
| TEA Diricinoleate/IPDI Copolymer Oleate | 2.0 | Same as on Left |
| Cetyl Alcohol and Ceteareth-20 | 2.0 | Cetyl Alcohol and Ceteareth 20 |
| Stearylamidopropyl Dimethyl Amine | 1.35 | Same as on Left |
| Dimethyl Lauramine Oleate | 1.0 | Dimethyl Lauramine Oleate |
| Propyl Paraben | 0.05 | Propyl Paraben |
| Fragrance | 0.2 | Fragrance |
| Citric Acid | 0.3 | Citric Acid |
| Total | 100.0 | |

Procedure:
1. To a clean reaction vessel add the above-listed first three ingredients to a blending vessel and with stirring heat to 75° C.
2. Slowly add the Hydroxyethyl Cellulose, maintain temperature and stir until a uniform solution is obtained.
3. Add the TEA Diricinoleate/IPDI Copolymer Oleate to the reaction product of step 2 at 75° C. and stir to uniformity.
4. In an auxiliary kettle, combine the Cetyl Alcohol and Ceteareth-20 Stearylamidopropyl Dimethyl Amine, Dimethyl Lauramine and Propyl Paraben and stir to uniformity and then add to the reaction product of step 3 in the primary mixing vessel.
5. Cool the reaction product of step 4 to 30° C. and add the Citric Acid and Fragrance.

Example 5

Low pH Glycolic Acid Solution

| RAW MATERIAL | %. WT. | INCI NAME |
|---|---|---|
| Water (Deionized) | 84.3 | Aqua |
| Phenoxyethanol (&) Methyl Paraben (&) Ethyl Paraben (&) Butyl Paraben | 0.5 | Same as on Left |
| Benzyl Alcohol | 0.50 | Benzyl Alcohol |
| Glycereth-7, Diglyceryl/Polyoxyethylene-15-Cocamine/IPDI Copolymer | 1.0 | Same as on Left |
| TEA Diricinoleate IPDI/Copolymer Dilinoleate | 0.5 | Same as on Left |
| Neopentyl Glycol Dicaprate | 4.7 | Neopentyl Glycol Dicaprate |
| Glyceryl Stearate (&) PEG-100 Stearate | 4.0 | Glyceryl Starate (&) PEG-100 Stearate |
| Castor Oil/IPDI Copolymer | 0.5 | Castor Oil/IPDI Copolymer |
| Glycolic Acid, 70% | 4.0 | Glycolic Acid |
| Triethanolamine, 99% | Q.S. | Triethanolamine |
| Total | 100.0 | |

Procedure:
1. To a clean vessel, add the Water and Phenoxyethanol Preservative as listed above and heat to 80° C.
2. Premix the Benzyl Alcohol, Glycereth-7 IPDI/Copolymer and TEA Diricinoleate IPDI/Copolymer Dilinoleate at 80° C. and slowly add to the above Water-Preservative blend of step 1.
3. Preblend the Neopentyl Glycol Dicaprate/Glyceryl Stearate (&) PEG-100 Stearate and Castor Oil IPDI/Copolymer at 80° C. and add to the above mixture of step 2 at 80° C. and stir until uniform.
4. Cool the batch of step 3 to 30° C. and add the Glycolic Acid solution to the batch and adjust pH with TEA to 4.0 to 4.5.

Example 6

Protective Hand Lotion

| RAW MATERIAL | %. WT. | INCI NAME |
|---|---|---|
| Hydrogenated Castor Oil/IPDI Copolymer | 3.0 | Same as on Left |
| Triple Pressed Stearic Acid | 7.5 | Triple Pressed Stearic Acid |
| TEA Diricinoleate IPDI/Copolymer Dilinoleate | 1.0 | Same as on Left |
| Dimethiconol IPDI/Copolymer | 4.0 | Dimethiconol IPDI/Copolymer |
| Cetyl Alcohol | 3.0 | Cetyl Alcohol |
| Petrolatum | 2.0 | Petrolatum |
| Sodium Stearate | 2.5 | Sodium Stearate |
| Phenoxyethanol and Chloroxylenol | 0.25 | Phenoxyethanol and Chloroxylenol |
| Water (Deionized) | 74.35 | Aqua |
| Sodium Hydroxide, 50% Aq Soln | 0.4 | Sodium Hydroxide |
| Total | 100.0 | |

Procedure:
1. To a clean reaction vessel add the first eight ingredients listed above and with moderate sweep, heat to 75° C. until uniform.
2. Add the water and sodium hydroxide amounts of step 1 to a reaction vessel, and then slowly add the water and sodium hydroxide to the above indicated blend and stir until emulsification is complete. Continue to stir with a slow sweep to a temperature of 25° C.

Example 7

Long Lasting Lipstick

| RAW MATERIAL | %. WT. | INCI NAME |
|---|---|---|
| Castor Oil IPDI/Copolymer | 9.05 | Castor Oil IPDI/Copolymer |
| Castor Oil | 38.80 | Castor OR |
| Diglyceryl Diisostearate | 14.0 | Diglyceryl Diisostearate |
| Isopropyl Palmitate | 10.0 | Isopropyl Palmitate |
| Synthetic Beeswax | 8.0 | Synthetic Beeswax |
| Carnauba Wax | 5.85 | Carnauba Wax |
| TEA Diricinoleate IPDI/Copolymer Dilinoleate | 0.2 | TEA Diricinolate IPDI/Copolymer |
| Propyl Paraben | 0.1 | Propyl Paraben |
| BHA | 0.5 | BHA |
| 60% TiO2 Paste in Castor Oil (Roller Mill) | 4.0 | Titanium Dioxide (and) Castor Oil |
| 50% D&C Red No. 6 in Castor Grind (Roller Mill) | 10.0 | D&C Red No. 6 in Castor Oil |
| Total | 100.0 | |

Procedure:
1. Place the first nine ingredients listed above into a heated kettle equipped with lightning mixture and heat thoroughly to 90° C.

2. Add the pigments to the reaction product of step 1 and continue heating at 90° C. until uniform.
3. Cool to 70–75° C. and fill.

Example 8

Vitamin E Cream

| RAW MATERIAL | %. WT. | INCI NAME |
|---|---|---|
| Water (Deionized) | 39.8 | Aqua |
| Propylene Glycol, USP | 4.0 | Propylene Glycol |
| Glycereth-7 Diglycerol PEG-15 Cocamine IPDI/Copolymer | 4.0 | Same as on Left |
| Phenoxyethanol (&) Methyl Paraben (&) Propyl Paraben (&) Butyl Paraben | .3 | Same as on Left |
| Allantoin | .2 | Allantoin |
| Triethanolamine, 99% | 1.20 | Triethanolamine |
| Vitamin E Acetate | 25.0 | Tocopheryl Acetate |
| Glyceryl Monostearate | 5.0 | Glyceryl Monostearate |
| Isopropyl Myristate | 6.0 | Isopropyl Myristate |
| Stearate Acid, T.P. | 3.0 | Stearic Acid |
| Castor Oil IPDI/Copolymer | 3.0 | Castor Oil IPDI/Copolymer |
| Glyceryl Tricaprylate/Tricaprate | 3.0 | Glyceryl Tricaprylate/Tricaprate |
| TEA Diricinoleate IPDI/Copolymer Dimer Dilinoleate | 3.0 | Same as on Left |
| Cetyl Alcohol | 2.5 | Cetyl Alcohol |
| Total | 100.0 | |

Procedure:
1. Add the above listed first six ingredients into a kettle and heat with high agitation to uniformity at 75–78° C.
2. Add the remaining ingredients listed above to a second kettle and heat with high agitation to 80° C.
3. Add the second mixture to the first mixture to achieve complete emulsification. Cool with a slow sweep to 25° C.

Example 9

Humectant Lotion

| RAW MATERIAL | %. WT. | INCI NAME |
|---|---|---|
| Water (Deionized) | 87.25 | Aqua |
| Triethanolamine, 99% | 0.6 | Triethanolamine |
| Glycereth-7-Diglycerol PEG-15 Cocamine Amine IPDI/Co-polymer | 0.1 | Same as on Left |
| Diglycerol | 1.5 | Diglycerol |
| Methyl Paraben | 0.15 | Methyl Paraben |
| TEA Diricinoleate IPDI/Copolymer Dimer Dilinoleate | 3.25 | Same as on Left |
| Glycereth-7-Hydroxystearate | 0.8 | Glycereth-7-Hydroxystearate |
| Stearic Acid | 2.0 | Stearic Acid |
| Castor Oil IPDI/Copolymer | 1.5 | Castor Oil IPDI/Copolymer |
| Cetyl Alcohol | 0.8 | Cetyl Alcohol |
| Propyl Paraben | 0.05 | Propyl Paraben |
| Sorbitol PEG (20) Monooleate | .75 | Sorbitol PEG (20) Monooleate |
| Glyceryl Monostearate and PEG-100 Stearate | 1.25 | Glyceryl Monostearate and PEG-100 Stearate |
| Total | 100.0 | |

Procedure:
1. Add the first five ingredients listed above into a clean, dry kettle and heat with high agitation to 80° C.
2. Add the remaining ingredients into a second kettle and heat with high agitation to 80° C.
3. Using a homogenizer, add the blend of step 2 to the blend of step 1 and heat until emulsification is complete.
4. With low agitation, cool the reaction product of step 3 to 25° C.

Example 10

Non-Aerosol Tube Shave Cream

| RAW MATERIAL | %. WT. | INCI NAME |
|---|---|---|
| Water (Deionized) | 70.90 | Aqua |
| Methyl Paraben | 0.20 | Methyl Paraben |
| Disodium EDTA | .10 | Disodium EDTA |
| Phenoxyethanol (&) Methyl Paraben (&) Isopropyl Paraben (&) Ethyl Paraben (&) Butyl Paraben | 0.30 | Same as on Left |
| Glycereth-7/Diglycerol PEG-(15) Cocamine/IPDI Copolymer | 3.5 | Same as on Left |
| Castor Oil PEG-100/IPDI Copolymer | 3.0 | Same as on Left |
| Carbomer | 6.00 | Carbomer |
| Triethanolamine, 99% | 1.00 | Triethanolamine |
| Water (Deionized) | 1.00 | Aqua |
| Stearic Acid, Triple Pressed | 8.00 | Stearic Acid |
| TEA Diricinoleate IPDI/Copolymer Dimer Dilinoleate | 2.00 | Same as on Left |
| Cocamide DEA | 1.50 | Cocamide DEA |
| Glycereth-7-12 Hydroxystearate | 1.00 | Glycereth-7-12 Hydroxystearate |
| Laureth-23 | 1.00 | Laureth-23 |
| Castor Oil/IPDI Copolymer | 0.5 | Castor Oil/IPDI Copolymer |

Procedure:
1. Heat the first 8 ingredients listed above to a clean mixing vessel and heat at 80° C. to clarity.
2. Add TEA and Water to the mixing vessel reactants of step 1.
3. Add the remaining ingredients listed above to the mixing vessel at 75° C. and stir until homogeneity is achieved. Cool to 30° C. with a sweep blade.

Example 11

Cationic Sunscreen

| RAW MATERIAL | %. WT. | INCI NAME |
|---|---|---|
| Water (Deionized) | 64.25 | Aqua |
| Phenoxyethanol (&) Methyl Paraben (&) Propyl Paraben (&) Butyl Paraben | 0.5 | Same as on Left |
| Glycereth-7/Diglycerol/PEG (15) Cocamine IPDI/Copolymer | 1.5 | Same as on Left |
| TEA Ricinoleate/Oleate IPDI Copolymer Dioleate | 0.5 | Same as on Left |
| Hydrogenated Castor Oil IPDI/Copolymer | 3.0 | Hydrogenated Castor Oil IPDI/Copolymer |
| Glyceryl Monostearate | 1.5 | Glyceryl Monostearate |
| Castor Oil IPDI/Copolymer | 0.25 | Castor Oil IPDI/Copolymer |
| Stearyl Alcohol (&) Ceteareth-20 | 2.0 | Stearyl Alcohol (&) Ceteareth-20 |
| Isostearyl Neopentanoate and Octyl Isononanoate | 8.0 | Same as on Left |
| Emulsifying Wax, NF | 0.5 | Emulsifying Wax |

-continued

| RAW MATERIAL | %. WT. | INCI NAME |
|---|---|---|
| Neopentyl Glycol Dioctanoate | 1.5 | Neopentyl Glycol Dioctanoate |
| Octyl Methoxycinnamate | 7.5 | Octyl Methoxycinnamate |
| Padimate 0 | 5.00 | Padimate 0 |
| Benzophenone-3 | 2.0 | Benzophenone-3 |
| PEG-40 Castor Oil IPDI/Copolymer | 2.0 | PEG-40 Castor Oil IPDI/Copolymer |
| Total | 100.0 | |

Procedure:
1. Heat the Water and Phenoxy Paraben Preservative listed above to 80° C. with agitation in a cleann reaction vessel.
2. Heat and blend the Glycereth IPDI/Copolymer and the Glycereth-7 IPDI/Copolymer to 70° C. and add to the blend of step 1.
3. Blend and heat the remaining components listed above in a separate clean blending vessel, heat to 80° C. and add this blend to the blend of step 1 and stir until uniform.
4. Cool with slow agitation to 30° C.

Example 12

Massage Oil

| RAW MATERIAL | %. WT. | INCI NAME |
|---|---|---|
| Mineral Oil | 70 | Mineral Oil |
| Octyl Palmitate | 15 | Ethylhexyl Palmitate |
| Diisopropyl Dimerate | 8.5 | Diisopropyl Dimerate |
| TEA Diricinoleate/IPDI Copolymer Dimer Dilinoleate | 1.5 | TEA Diricinoleate/IPDI Copolymer Dimer Dilinoleate |
| Isopropyl Isostearate | 5 | Isopropyl Isostearate |
| Total | 100.0 | |

Procedure:
1. Blend all ingredients listed above in a clean reaction vessel at 40–45° C. for 10 minutes with slow agitation until uniform.
2. Cool the reaction mixture of step 1 to room temperature.

Example 13

Vitamin Enriched Barrier Cream

| RAW MATERIALS | %. Weight. |
|---|---|
| Water (Deionized) | 83.0 |
| Magnesium Aluminum Silicate | 0.8 |
| Carbomer | 0.3 |
| Glycerin | 2.0 |
| Butylene Glycol | 2.0 |
| Cetyl Alcohol | 0.5 |
| Glyceryl Monostearate, SE | 2.0 |
| Caprylic/Capric Triglyceride | 2.0 |
| Isononyl Isononanoate | 2.0 |
| TEA Diricinoleate/IPDI Copolymer Dimer Dilinoleate | 1.0 |
| Bois Oil | 0.5 |
| Steareth-2 | 0.95 |
| Steareth 21 | 0.95 |
| d-Panthenol | 1.0 |
| Vitamin E Acetate | 0.5 |
| Vitamin E Palmitate | 0.5 |
| Preservative, Fragrance | Q.S. |
| Total | 100.0 |

Procedure:
1. In a clean reaction vessel, heat the amount of water indicated above to 75–80° C., slowly add the Magnesium Aluminum Silicate amount listed above and mix until hydrated.
2. Add to the reaction mixture of step 1 the above ingredients and amounts listed as "B" and stir the resultant reaction mixture until uniform.
3. In a separate vessel, heat the reactants and amounts listed above as "C" to 75–80° C. until uniform and slowly add to the reaction mixture of step 2 with good agitation.
4. Cool the reaction mixture of step 3 with mixing and adjust pH to 5.8±0.3.

Example 14

Shine Enhancing Pomade

| RAW MATERIAL | %. WT. |
|---|---|
| Petrolatum | 69.50 |
| Microcrystalline Wax | 12.0 |
| Polyisobutene | 7.00 |
| Phenyl Trimethicone | 6.00 |
| TEA Diricinoleate IPDI/Copolymer Diricinoleate | 1.00 |
| Castor Oil IPDI/Copolymer | 1.80 |
| Safflower Seed Oil | 1.00 |
| Octyl Methoxycinnamate | 1.00 |
| Propyl Paraben | 0.20 |
| Fragrance | 0.50 |
| Total | 100.0% |

Procedure:
1. To a clean reaction vessel equipped with a propeller-type mixer, add petrolatum in the amount listed above and heat to 75° C.
2. Add remaining ingredients and amounts listed above to the reaction product of step 1, one at a time in the order listed above or in any other order and mix until clear.
3. Pour into suitable containers.

It is to be understood by those skilled in the art that the foregoing description and examples are merely illustrative of the present invention, and should in no way be intrepreted as limiting the scope of the present invention. Variations of the detail presented herein may be made without departing from the spirit and scope of the present invention as defined by the following claims.

What is claimed is:

1. A composition comprising a polymeric urethane ester tertiary amine salt or a mixture of a polymeric urethane ester tertiary amine and a salt thereof obtained by reacting an organic acid with a urethane adduct which is formed from the reaction of a diisocyanate with a monomeric or polymeric mono-, di-, or tri-ester of a trialkanolamine.

2. The composition of claim 1 wherein:
   (a) the organic acid is selected from the group consisting of carboxylic acids, fatty acids, $C_6$ through $C_{22}$ isomeric acids, aromatic acids, phenylstearic acids, dimer acids and $C_{36}$ to $C_{48}$ trimer acids, including oleic acid, stearic acid, palmitic acid, coconut fatty acid, lauric acid, myristic acid, aradonic acid, erusic acid, ricinoleic acid, ricinleic acid, 12-hydroxystearic acid, caproic acid, capric acid, mono-ricinoleic, di-ricinoleic, mono-12-hydroxystearic, di-12-hydrostearic, monobehenic, dibehenic, monooleic, di-oleic, mono-soya, di-soya, mono-safflower, di-safflower, mono-sunflower, di-sunflower, mono-myristic and di-myristic acids;
   (b) the diisocyanate is selected from the group consisting of, isophorone diisocyanate, m-phenylenediisocyanate, p-phenylene diisocyanate, 4,4-butyl-m-phenylene diisocyanate, 4-methoxy-m-phenylene diisocyanate, 4-phenoxy-m-phenylene diisocyanate, 4-chloro-m-phenylene diisocyanate, toluenediisocyanate, m-xylylenediisocyanate, p-xylylenediisocyanate, 1,4-napthalenediisocyanate, cumene-14,-diisocyanate, durenediisocyanate, 1,5-napthylenediisocyanate, 1,8-napthylenediisocyanate, 1,5-tetrahydronapthylenediisocyanate, 2,6-napthylenediisocyanate, 1,5-tetrahydronapthylenediisocyanate; p,p-diphyleneduisocyanate; 2,4-diphenythexane-1,6-diisocyanate; methylenediisocyanates; ethylenediisocyanates; trimethylenediisocyanate, tetramethylenediisocyanate, pentamethylenediisocyanate, hexamethylenediisocyanate, nonamethylenediisocyanate, decamethylenediisocyanate, 3-chloro-trimethylenediisocyanate and 2,3-dimethyltetramethylene diisocyanates; and
   (c) the trialkanolamine is selected from the group consisting of triethanolamine, triisopropanolamine, triisobutanolamine, triisopentanolamine, triisohexanolamine, diethanolmonoisopropanolamine, monoethanoldiisopropanolamine, monoethanoldiisobutanolamine and their analogues and was esterified by reaction with one or more organic acids.

3. A composition of claim 1 made by reacting a urethane adduct with a mono-, di- or tricarboxylic acid wherein the urethane adduct is formed by reacting a polymeric di- or tri-ester with a diisocyanate and the polymeric di- or tri-ester is formed by esterifying triethanolamine with a $C_6$ to $C_{48}$ long chain fatty acid.

4. A composition of claim 1 made by reacting a urethane adduct with a mono-, di- or tricarboxylic acid wherein the urethane adduct is formed by reacting a monomeric di- or tri-ester with a diisocyanate and the monomeric di- or tri-ester is formed by esterifying triethanolamine with a $C_6$ to $C_{48}$ long chain fatty acid.

5. A composition of claims 3 or 4, wherein the diisocyanate is IPDI.

6. A composition of claim 1 formed by reacting the urethane adduct with a linear, isomeric, aromatic, dimerized, trimerized, alpha hydroxy or beta hydroxy acid $C_6$ through $C_{36}$ fatty acid.

7. A composition comprising a polymeric urethane ester tertiary amine salt or a mixture of a polymeric urethane ester tertiary amine and a salt thereof formed by reacting triethanolamine linoleate-ricinoleate diester IPDI copolymer with a mono-, di- or tricarboxylic acid.

8. A composition comprising a polymeric urethane ester tertiary amine salt or a mixture of a polymeric urethane ester tertiary amine and a salt thereof formed by reacting a triethanolamine diricinoleate diester IPDI copolymer with a mono-, di- or tricarboxylic acid.

9. A composition comprising a polymeric urethane ester tertiary amine salt or a mixture of a polymeric urethane ester tertiary amine and a salt thereof formed by reacting a triethanolamine hydroxstearate diester IPDI copolymer with a mono-, di- or tricarboxylic acid.

10. The composition of claims 7, 8 or 9, wherein the mono-, di- or tricarboxylic acid is a $C_6$ to $C_{48}$ fatty acid.

11. A composition comprising a polymeric urethane ester tertiary amine salt or a mixture of a polymeric urethane ester tertiary amine and a salt thereof made by reacting a urethane adduct with a mono-, di-, tri- or tetracarboxylic acid wherein the urethane adduct is formed by reacting a monomeric or polymeric mono-, di- or tri-ester with a diisocyanate, and wherein the monomeric or polymeric mono- or di-ester is formed by reacting a trialkanolamine with an organic acid.

12. The composition of claim 11, wherein:
the trialkanolamine has the formula (I):

where $R_a$, $R_b$ and $R_c$ are the same or different and are substituted or unsubstituted, branched or unbranched alkyl groups derived from an alkanolamine;
the diisocyanate has the formula $R_f$—$(N=C=O)_2$, where $R_f$ is a saturated, unsaturated, aromatic or halogen substituted linear, cyclic, aromatic or branch-chained hydrocarbon;
the trialkanolamine is reacted with an organic acid selected from the group consisting of long chain fatty acids selected from the group consisting of $C_2$ to $C_{36}$ dimer and trimer acids, alpha hydroxy acids, beta hydroxy acids, linear acids, isomeric acids and phenylstearic acids, linear $C_6$ through $C_{22}$ fatty acids, $C_6$ through $C_{22}$ isomeric acids, aromatic acids, phenylstearic acids, dimer acids, and trimer acids which range from 36 through 48 carbon chain lengths; and
the urethane adduct is reacted with a mono-, di-, or tri-carboxylic acid of the formula $R_g$ $(OOH)_n$, where n is 1 to 3 and $R_g$ is selected from a $C_4$ through $C_{48}$ (preferably, $C_6$ through $C_{22}$) linear or branched-chained, cylic, saturated or unsaturated hydrocarbon groups which are substituted, monomeric or dimeric or an aromatic group, including a phenyl or benzyl group or substituted phenyl or benzyl group, an alkylphenyl, alkylbenzyl, substituted alkylphenyl or alkylbenzyl group and may contain one or more ester or hydroxyl groups or urethane linkages.

13. The composition of claim 12, wherein $R_a$, $R_b$, and $R_c$ are $(CH_2)_2$, the organic acid is selected from the group consisting of $C_6$ through $C_{22}$ fatty acids, and $R_f$ is an isophorone group.

14. A composition comprising a polymeric urethane ester tertiary amine salt or a mixture of a polymeric urethane ester tertiary amine and a salt thereof made by reacting a polymeric urethane adduct and either a mono-, di- or tricarboxylic acid, wherein the polymeric urethane adduct is formed by the reaction of a diisocyanate with an adduct formed by esterifying mono- or diesters of alpha hydroxy and beta hydroxy acids to a mono or difunctionality with a trialkanolamine.

15. The composition of claim 14, wherein the diisocyanate is isophrone diisocyanate and the alpha hydroxy and beta hydroxy acids are selected from the group consisting of lactic, hydroxy caprylic, hydroxy capric, and salicylic acids.

16. The composition of claim 11, wherein the monomeric or polymeric mono-, di-, or tri-ester is formed at an esterification reaction temperature of about 30° to about 300° C. and an esterification reaction pressure of about 3 to about 3,000 mbar, the polymeric urethane adduct is formed at a reaction temperature of between about 50° C. to about 150° C., and the polymeric urethane ester tertiary amine is formed at a reaction temperature of around 30° C. to around 150° C.

17. The composition of claim 11, wherein the molar ratio of polymeric urethane adduct to mono-, di- or tricarboxylic acid is less than or equal to about one.

18. The composition of claim 1 or 11, wherein the polymeric urethane ester tertiary amine salt or said mixture is made one-pot.

19. The composition of claim 1 or 11 made by:
(a) reacting a trialkanolamine with an organic acid to form a monomeric or polymeric mono-, di-, or tri-ester;
(b) reacting the monomeric or polymeric mono-, di-, or tri-ester formed in step (a) with a diisocyanate to form a polymeric urethane adduct; and
(c) reacting the polymeric urethane adduct formed in step (b) with a mono-, di- or tricarboxylic acid, at a molar ratio of polymeric urethane adduct to mono, di or tricarboxylic acid of less than or equal to about one.

20. A method of making a polymeric urethane ester tertiary amine salt or a mixture of a polymeric urethane ester tertiary amine and a salt thereof comprising:
reacting a polymeric urethane adduct with a mono-, di-, or tri-carboxylic acid wherein the polymeric urethane adduct is formed by reacting a monomeric or polymeric mono-, di-, or tri-ester with a diisocyanate, and wherein the monomeric or polymeric mono-, di-, or tri-ester is formed by reacting a trialkanolamine with an organic acid.

21. The method of claim 20, wherein:
(a) the organic acid is selected from the group consisting of oleic acid, stearic acid, palmitic acid, coconut fatty acid, lauric acid, myristic acid, aradonic acid, erusic acid, ricinoleic acid, ricinleic acid, 12-hydroxystearic acid, caproic acid, capric acid, mono-ricinoleic, di-ricinoleic, mono-12-hydroxystearic, di-12-hydrostearic, monobehenic, dibehenic, monooleic, di-oleic, mono-soya, di-soya, mono-safflower, di-safflower, mono-sunflower, disunflower, mono-myristic and di-myristic acids;

(b) the diisocyanate is selected from the group consisting of isophorone diisocyanate, m-phenylenediisocyanate, p-phenylene diisocyanate, 4,4-butyl-m-phenylene diisocyanate, 4-methoxy-m-phenylene diisocyanate, 4-phenoxy-m-phenylene diisocyanate, 4-chloro-m-phenylene diisocyanate, toluenediisocyanate, m-xylylenediisocyanate, p-xylylenediisocyanate, 1,4-napthalenediisocyanate, cumene-14,-diisocyanate, durenediisocyanate, 1,5-napthylenediisocyanate, 1,8-napthylenediisocyanate, 1,5-tetrahydronapthylenediisocyanate, 2,6-napthylenediisocyanate, 1,5-tetrahydronapthylenediisocyanate; p,p-diphylenediisocyanate; 2,4-diphenythexane-1,6-diisocyanate; methylenediisocyanates; ethylenediisocyanates; trimethylenediisocyanate, tetramethylenediisocyanate, pentamethylenediisocyanate, hexamethylenediisocyanate, nonamethylenediisocyanate, decamethylenediisocyanate, 3-chloro-trimethylenediisocyanate and 2,3-dimethyltetramethylene and diisocyanates; and (c) the trialkanolamine is selected from the group consisting of triethanolamine, triisopropanolamine, triisobutanolamine, triisopentanolamine, triisohexanolamine, diethanolmonoisopropanolamine, monoethanoldiisopropanolamine, monoethanoldiisobutanolamine and their analogues.

22. A personal care product composition to be used in contact with the skin, hair or nails, said personal care product comprising a mixture of effective amounts of components selected from the group consisting of water, solvents, emollients, humectants, emulsifiers, surfactants, thickeners, coloring agents, preservatives and fragrances, said composition further comprising an effective amount of a composition acording to claim 1 or 11.

23. The personal care product composition of claim 22, wherein the personal care product composition is a lipstick, a detergent, a hair colorer, a liquid soap, a bar soap, a cream, a lotion, a bath gel, a hand cleaner, a conditioner, a shampoo, a shaving cream, a detangler for hair or a fabric softener.

24. A method of enhancing or modifying at least one of the characteristics of a personal care product selected from the group consisting of skin and hair adherence, viscosity, substantivity, conditioning, irritation and wetting comprising adding to said personal care product an effective amount of a composition acording to claim 1 or 11.

25. The method of claim 24, wherein the composition comprises the reaction product of a $C_6$ to $C_{36}$ fatty acid with a urethane adduct selected from the group consisting of triethanolamine linoleate-ricinoleate diester IPDI copolymer, triethanolamine diricinoleate diester IPDI copolymer or triethanolamine hydroxstearate diester IPDI copolymer.

* * * * *